(12) United States Patent
Reuter

(10) Patent No.: US 10,182,856 B2
(45) Date of Patent: Jan. 22, 2019

(54) OSTEOSYNTHESIS PLATE AND SYSTEM FOR OSTEOSYNTHESIS

(71) Applicant: aap Implantate AG, Berlin (DE)

(72) Inventor: Andreas Reuter, Potsdam (DE)

(73) Assignee: aap Implantate AG, Berlin (DE)

( * ) Notice: Subject to any disclaimer, the term of this patent is extended or adjusted under 35 U.S.C. 154(b) by 52 days.

(21) Appl. No.: 14/787,410

(22) PCT Filed: May 13, 2014

(86) PCT No.: PCT/EP2014/059726
§ 371 (c)(1),
(2) Date: Oct. 27, 2015

(87) PCT Pub. No.: WO2014/184175
PCT Pub. Date: Nov. 20, 2014

(65) Prior Publication Data
US 2016/0066969 A1   Mar. 10, 2016

(30) Foreign Application Priority Data

May 13, 2013   (DE) .................. 10 2013 104 887

(51) Int. Cl.
*A61B 17/56* (2006.01)
*A61B 17/58* (2006.01)
(Continued)

(52) U.S. Cl.
CPC ...... *A61B 17/8061* (2013.01); *A61B 17/1728* (2013.01); *A61B 17/80* (2013.01); *A61B 17/82* (2013.01)

(58) Field of Classification Search
CPC . A61B 17/80; A61B 17/8004; A61B 17/8014; A61B 17/8061; A61B 17/82; A61B 17/1728
(Continued)

(56) References Cited

U.S. PATENT DOCUMENTS

2006/0089648 A1\* 4/2006 Masini ............... A61B 17/1615
606/71
2006/0100625 A1   5/2006 Ralph et al.
(Continued)

FOREIGN PATENT DOCUMENTS

CN         101056590 A    10/2007
DE         19802229 A1    9/1999
(Continued)

OTHER PUBLICATIONS

DE102010041564A1 translation attached.\*
(Continued)

*Primary Examiner* — Si Ming Ku
(74) *Attorney, Agent, or Firm* — Kaplan Breyer Schwarz, LLP

(57) ABSTRACT

An osteosynthesis system includes a bone plate and a segment. The bone plate includes a plurality of passages for bone screws and at least one web. The segment includes at least one passage for a screw. The segment has a clip-like configuration and can be snapped onto the web of the bone plate. The segment also has an upper half and a lower half and is fastened on the web of the bone plate with a force-locked connection by moving the upper and lower halves toward each other. The upper and the lower halves are moved towards each other by introducing a screw into the at least one passage of the segment.

12 Claims, 22 Drawing Sheets

Figure 1:
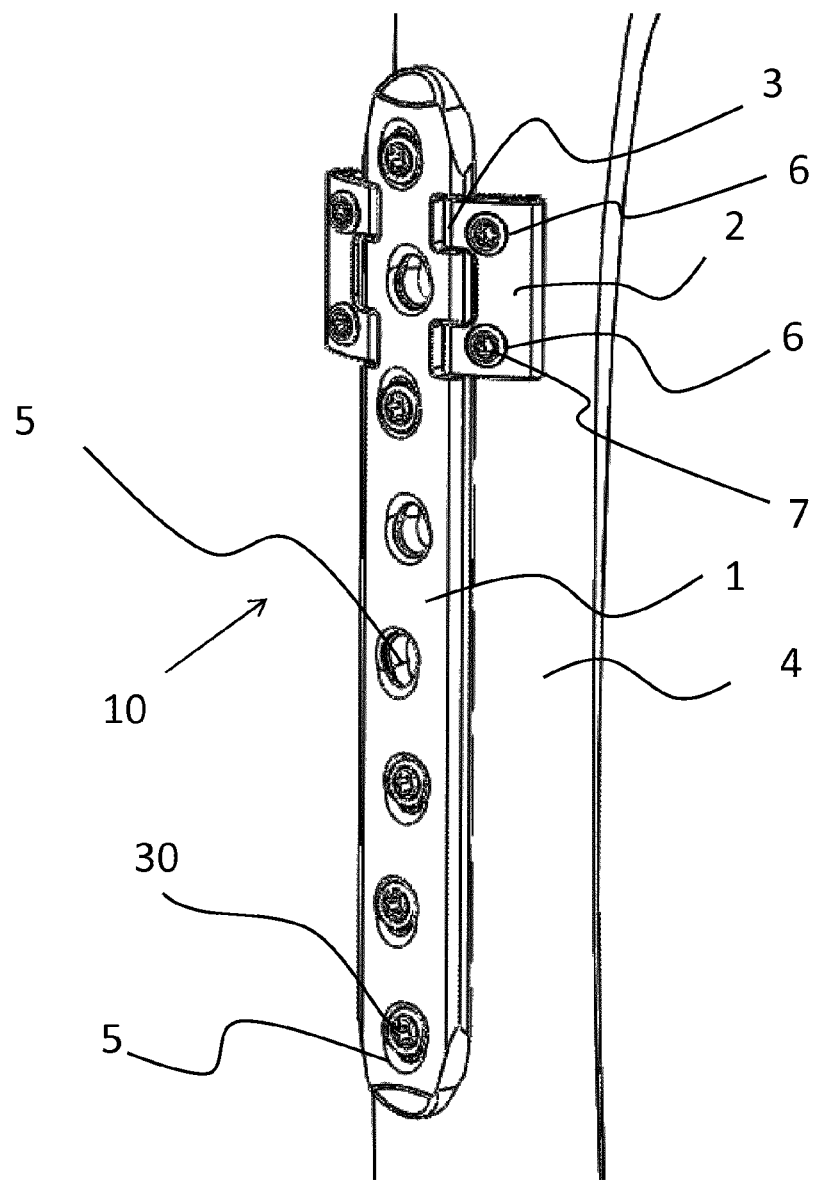

(51) Int. Cl.
*A61B 17/80* (2006.01)
*A61F 2/30* (2006.01)
*A61B 17/17* (2006.01)
*A61B 17/82* (2006.01)

(58) Field of Classification Search
USPC .................. 606/71, 74, 324, 75, 246–279
See application file for complete search history.

(56) References Cited

U.S. PATENT DOCUMENTS

| | | | |
|---|---|---|---|
| 2006/0142767 | A1 | 6/2006 | Green et al. |
| 2007/0233111 | A1* | 10/2007 | Orbay ................ A61B 17/1728 606/286 |
| 2009/0118768 | A1 | 5/2009 | Sixto, Jr. et al. |
| 2010/0262194 | A1 | 10/2010 | Wagner et al. |
| 2012/0089144 | A1 | 4/2012 | Murner et al. |
| 2013/0090695 | A1* | 4/2013 | Bernstein ............ A61B 17/808 606/281 |

FOREIGN PATENT DOCUMENTS

| | | | | |
|---|---|---|---|---|
| DE | 202008014358 | U1 | 9/2009 | |
| DE | 102010025001 | A1 | 12/2011 | |
| DE | 102010041564 | A1 * | 3/2012 | ......... A61B 17/7059 |
| EP | 1393689 | A2 | 3/2004 | |
| FR | 2956972 | A1 | 9/2011 | |
| GB | 2422783 | A | 9/2006 | |
| JP | 2560207 | B2 | 12/1996 | |
| JP | 2003024344 | A * | 1/2003 | ........... A61B 17/746 |
| RU | 2065733 | C1 | 8/1996 | |
| RU | 2206290 | C2 | 6/2003 | |
| RU | 2218123 | C2 | 11/2009 | |
| SU | 1311727 | A1 | 5/1987 | |
| WO | 9937231 | A1 | 7/1999 | |
| WO | 02076317 | A1 | 10/2002 | |
| WO | 2004045389 | A2 | 6/2004 | |
| WO | 2006049998 | A1 | 5/2006 | |
| WO | 2011042407 | A1 | 4/2011 | |
| WO | 2012135860 | B2 | 10/2012 | |
| WO | 2013029188 | A1 | 3/2013 | |

OTHER PUBLICATIONS

JP2003024344A and DE102010041564A1 translations attached.*
Nora Linder, "International Preliminary Report on Patentability"; English Translation; issued in International Application No. PCT/EP2014/059726 dated Nov. 26, 2015.
"Chinese Office Action", issued in counterpart Chinese Application No. 201480027324.2, dated May 27, 2017, 20 pp.
"German Office Action", issued in related German Application No. 102013104887.0, dated Nov. 29, 2013.
"International Search Report and Written Opinion" issued in related International Application No. PCT/EP2014-059726, dated Jul. 7, 2014.
"Japanese Office Action", Japanese Patent Application 2016-513330, dated Aug. 25, 2017, 14 pp.
"Russian Office Action", Related Russian Patent Application No. 2015153423, dated Jan. 15, 2018, 21 pp.
Korean Office Action, Counterpart Korean Patent Application 10-2015-7034926, dated Apr. 16, 2018, 23 pp.

* cited by examiner

OSTEOSYNTHESIS PLATE AND SYSTEM FOR OSTEOSYNTHESIS

FIELD OF THE INVENTION

The invention relates to an osteosynthesis plate, to a segment for an osteosynthesis plate, and to a system for osteosynthesis.

More particularly the invention relates to a system for osteosynthesis of periprosthetic fractures and for providing support for fractures of osteoporotic bones.

BACKGROUND OF THE INVENTION

Systems for osteosynthesis that comprise a bone plate have been known.

Published patent application DE 10 2010 025001 A1 discloses a bone plate, for example.

Such a bone plate is usually made of a rigid material, in particular metal or a surgical stainless steel. The bone plate has passages into which screws can be introduced.

Mostly, screws are used for fastening the bone plate to the bone fragments. For reliably anchoring the screws, they should be placed bicortically. For this purpose, an osteosynthesis system comprises screws of various lengths.

Problems are encountered in the treatment of periprosthetic fractures. In this case it is mostly impossible for the screw to be placed bicortically, since the medullary canal is blocked by the prosthesis.

Therefore, monocortical screws are often used in this case. However, such a connection is far less mechanically resistant. In many cases, even monocortical screws cannot be used due to the small distance between the bone plate and the prosthesis. Therefore, cerclage wires are employed which are wrapped around the bone. Such attachment also fails to provide great mechanical stability and may cause lesions of the periosteum.

Published patent application US 2010/0262194 A1 discloses an osteosynthesis system comprising auxiliary components attachable to the bone plate, through which bone screws can be introduced from a lateral side in order to be directed past the medullary canal.

However, this system is rather inconvenient, fails to sufficiently adapt to the respective anatomy of the patient in many cases, and is bulky.

OBJECT OF THE INVENTION

Therefore, the invention is based on the object to provide an osteosynthesis plate and a system for osteosynthesis which can be easily adapted to the respective bone shape of the patient, in particular for being used in the treatment of periprosthetic fractures.

SUMMARY OF THE INVENTION

The object of the invention is already achieved by an osteosynthesis plate and by a system for osteosynthesis according to the illustrative embodiment of the present invention.

The invention relates to an osteosynthesis plate comprising a first segment and a second segment, and wherein at least one of the segments, preferably both segments, have a hole for passing a bone screw therethrough.

Instead of a passage, one of the segments, in particular the second segment, may as well have a recess or a projection, in particular an eyelet or an edge-side recess to serve as a bearing point for a cerclage cable, for example.

According to the invention, the second segment is releasably connectable to the first segment.

That means, the first segment can be connected to the second segment, in particular by a plug-in connection, snap connection, or slide-on connection. This permits to attach or remove segments depending on the application location, so that the basic shape of the osteosynthesis plate as defined by the segments can be modified by adding or removing segments.

Preferably, the segments are attachable without using tools, in particular it is preferred not to use any screws for interconnecting the segments.

Furthermore, the angle in which the first and second segments are arranged relative to each other can be modified. Angle here refers to the angle between the surfaces of the two segments. If a surface is curved, any tangent plane to this surface may be used as a reference.

Preferably, the angle can be modified perpendicular to the plane of the plate, i.e. perpendicular to the surface or to a tangent plane of a curved surface.

Preferably, the angle can be varied within a range of at least 10°, preferably within a range of at least 20°.

Thus, it is possible that the first and second segments form parts of an osteosynthesis plate and that the segments adapt to the contour of the bone.

Preferably, the segments are movable along an axis to modify the angle between the segments.

Preferably, the second segment is pivotally linked to the first segment. In this case, the pivot axis substantially extends in parallel to a surface of the first and of the second segment, so that the second segment can be moved like a wing relative to the first segment.

In particular, the first and second segments are pivotally connected by means of a hinge.

Thus, the two segments of the osteosynthesis plate are connected along one edge so as to be movable in at least one, preferably in exactly one degree of freedom.

This enables the segments which are made of rigid material to conform to the shape of the bone.

At the same time a hinge-like connection with only one degree of freedom ensures that the first segment can be moved relative to the second segment in not more than one direction, if any.

This direction of movability may extend in parallel to the fracture, for example, so that a firm connection is provided in the direction transversely to the fracture in which the bone plate is intended to stabilize the fracture.

In particular it is contemplated that the first segment is provided in form of an elongated bone plate having a plurality of passages.

Further segments may be movably attached to the elongated segment that defines a bone plate in a manner so as to protrude laterally from the main extension direction of the first segment.

Preferably, the first segment has a plurality of mounting sites at which further segments may be movably attached. Depending on the anatomical conditions of the patient it is thus possible to virtually extend the bone plate to the lateral sides, so that fixing screws may be introduced adjacent the bone plate, for example in order to avoid the medullary canal upon fixing, or to be able to tighten the screws in locations of the bone which exhibit a more stable bone structure.

In one embodiment of the invention the first and second segments are configured so that they can be separated and/or connected without the need of tools.

In particular it is contemplated that the first segment which is configured as a bone plate and has a plurality of passages, has a plurality of webs for receiving a hinge opening.

Web refers to a portion of the bone plate which may serve as a bearing for a hinge.

Furthermore, it is in particular contemplated that the second segment includes a clamp-shaped or hook-shaped hinge opening which serves to attach the latter to the first segment.

In the case of a simple hook, according to a preferred embodiment of the invention it is contemplated that the hook is formed in a manner so that the second segment is held with positive fit with the bone plate tightly bearing on the bone. Thus, the hinge-like connection can be easily released in an assembled state. This is for example possible when the segments are arranged relative to each other in a certain angle that does not correspond to the angle of the engaged state. If now the segments are turned relative to each other, the hook will engage behind the web of the first segment so that the segments are coupled like a hinge.

It is furthermore conceivable that a segment has a clip-like configuration, so that it can be urged onto a web and is latched or at least clamped thereon.

This preferred embodiment of the invention has the advantage that the two segments are connected to each other at any angle, even in the non-applied state. On the other hand, a clip-type connection can be easily disengaged by the user.

To be able to provide such a clip-like connection, the respective segment, preferably the second segment, may be U-shaped, with the two halves of the U-shaped configuration being resilient so that a clip-like hinge wing allows the segment to be attached by spreading the U-shaped configuration, which then snaps into place.

In one modification of the invention, a plurality of segments, i.e. at least three segments, may be stringed together.

To this end, it is especially contemplated that the second segment comprises both a hinge opening and a web for attaching another hinge segment. In this way, the fixing region may be expanded sidewards by juxtaposing segments which follow the contour of the bone like a caterpillar track. Thus, the osteosynthesis plate formed by the segments will be configured like a link chain.

It is conceivable that the bone is entirely or partially wrapped by means of such a link-like chain of segments.

The passages of the first and/or second segments are preferably at least partially threaded in order to provide an angularly stable connection with an appropriate screw that has a threaded head.

In one refinement of the invention, the first and second segments are adapted to be fixable relative to one another. This is to say that the hinge-like connection of the segments can be locked in the assembled state, so that the segments cannot be moved relative to each other, or only with great effort.

This may in particular be achieved if one segment has a U-shaped design and upon screwing in the bone screw the halves defining the U are pressed against each other, so that a force-locked connection on the web is produced.

The invention further relates to a segment for an osteosynthesis plate, in particular for an osteosynthesis plate as described above.

The segment has a web for receiving a hinge opening. In particular, the web is pin-shaped and is located in a recess of the bone plate, so that there is enough space around the web to movably accommodate a hinge opening. Furthermore, in one embodiment, the material of the segment at the ends of the web serves as a stop in an axial direction, i.e. in the main extension direction of the web.

In one embodiment, the web of a segment is formed integrally, that is to say the web is produced by a machining process from a solid material, for example.

In particular it is contemplated that all segments of the osteosynthesis plate are integrally formed. This facilitates manufacturing from biocompatible material and avoids the risk that components may detach from the osteosynthesis system and might remain in the patient's body under certain circumstances. Preferably, the segments are produced from a solid material such as titanium by a machining process.

In an alternative embodiment, the web may be formed by a pin mounted in the segment. Manufacturing of this variant is usually less expensive and the web may be made of a different material than the rest of the segment.

The hinge segments have an upper surface and a lower surface, wherein in the context of the invention the lower surface refers to the surface which faces the bone during the intended use.

In order to approach the contour of the bone, the lower surface preferably has a concave shape. The upper surface may be convex.

Furthermore, the segment may comprise at least two spaced-apart hinge openings. In this manner, a segment may be attached to at least two webs of the other segment.

This enables a more stable mechanical connection, since in this case the webs can be made shorter and thus the risk of breakage of the web is reduced. Moreover, in case of clip-like segments engagement thereof is facilitated.

In one refinement of the invention, the segment is U-shaped, and the recess between an upper half and a lower half enlarges to define a resilient portion on a closed side of the U.

So the height of the recess between the two halves of the segment increases at the end of the U-shaped portion. Seen in cross section, this allows the material to extend from the upper half downwards around a corner. This portion with changing direction of extension is formed of thinner material than the portions of the lower and upper halves in front thereof and thus has a resilient behavior due to its length, inter alia.

For fixing the segments when tightening a bone screw, one segment may be U-shaped and may have a passage, which passage is threaded at a lower end intended to rest against a bone.

Preferably, an opposite upper end of the passage does not have means adapted to engagement a thread of the bone screw. Specifically, the upper end of the passage has smooth walls.

A corresponding bone screw has a threaded portion on the head and a bearing surface above the threaded portion, in particular with a conical or spherical shape.

If now the head thread engages the threaded portion of the segment, the U-shaped segment will be pressed together due to the smooth-walled shape above the threaded portion of the head and will become clamped on the web of the adjacent segment.

A thread refers to a formation which enables a screw-type connection. This may even encompass a thread that is cut by the screw itself or which consists of thread segments, in particular in order to vary the angle of the screw to be introduced. In this manner, a polyaxial angularly stable connection is made possible.

A smooth-walled formation in the context of the invention refers to a configuration in which no screw connection is resulting. In the simplest case the smooth-walled formation may be a smooth surface, against which a screw head will bear. Preferably, however, the smooth-walled surface is tapering, in particular with a conical or spherical taper.

The invention permits to provide an osteosynthesis system comprising an osteosynthesis plate as described above and a bone screw which is designed such that upon tightening of the bone screw the segments of the osteosynthesis plate are fixed relative to each other.

The invention further relates to an osteosynthesis system comprising a bone plate or a segment of a bone plate. The bone plate or the segment has two layers, at least in portions thereof, and has an upper half and a lower half. The upper and lower halves are preferably resiliently connected to each other and thus are spaced apart by a gap, at least in an initial state. The segment or the bone plate has at least one passage that extends through the upper and the lower half.

The passage allows to introduce a bone screw.

The passage has a lower half which is provided with a thread, at least in portions thereof.

In the context of the invention, a thread refers to any engagement formation which is adapted to provide a positive locking connection with a corresponding formation of a bone screw in an axial direction.

Thus, the thread may for example merely be formed as a ridge.

Furthermore, it is conceivable that the thread is being cut into the material only when introducing a screw.

The minimum diameter of the passage in the lower half is smaller than the minimum diameter of the passage in the upper half.

The osteosynthesis system further comprises a bone screw having a thread which is adapted to be screwed into a bone.

This thread may in particular be a thread having a self-tapping tip.

Furthermore, the bone screw has a screw head.

The screw head has a formation enabling engagement of a handling tool by means of which the bone screw is screwed in.

Moreover, the screw head has a bearing surface. The bearing surface is configured so as to abut adjacent to or in the upper passage.

In the simplest case, the bearing surface may be a flat surface that will abut on the upper surface of the segment or of the bone plate next to the passage.

Preferably, however, the bearing surface is tapering, in particular spherically or conically, and will abut at a corresponding tapering surface of an upper portion of the passage.

When the bone screw is introduced the head thread will first pass through the upper portion of the passage.

Since the upper portion of the passage has a larger diameter than the head thread, this will not result in an axial positive interlocking connection.

As the screw is further introduced, the head thread will engage the thread in the lower half of the passage.

Then, or at the same time, the bearing surface of the screw head will abut on the upper half of the segment or of the bone plate, so that when screwing continues the two halves of the segment or of the bone plate will be drawn together.

By urging the two halves towards each other, they may clamp on another segment, for example.

However, it is also conceivable to clamp another component, such as a cerclage cable, between the segments.

The osteosynthesis system may moreover comprise a drill sleeve which can be introduced into the passage.

Such drill sleeves are known per se. They are used in order to produce a channel in the bone by means of a drill before the bone screw is screwed into the bone. Often, such drill sleeves are part of a targeting device which permits to precisely align the intended direction of extension of the channel prior to drilling.

The invention relates to a drill sleeve by means of which the halves of the bone plate or of the segment can be moved toward each other, i.e. pressed together.

For this purpose, the drill sleeve may comprise a thread which is screwed into the lower half.

Furthermore, a locking nut may be arranged above the thread. By tightening the locking nut, the halves of the segment or of the bone plate are pressed together.

In this manner it is in particular possible by means of the drill sleeve to fix a first and a second segment relative to each other with angular stability.

The invention relates to an osteosynthesis system comprising a drill sleeve that is introducible by screwing.

The drill sleeve is adapted such that when screwed in the lower end of the drill sleeve abuts and is supported on the bone. This permits to adjust the spacing between the segment or bone plate and the bone depending on the extent to which the drill sleeve is screwed in.

In case of an osteosynthesis plate that comprises at least two segments as described above, the angle between the segments may be easily adjusted in this manner.

The invention further relates to a bone screw which is in particular adapted for an osteosynthesis system as described above.

The bone screw has a thread for screwing into a bone, and a screw head having a bearing surface. Between the thread for screwing into the bone and the screw head, a head thread is provided which has a maximum diameter between the maximum diameter of the thread for screwing into the bone and that of the screw head.

DETAILED DESCRIPTION

The subject matter of the invention will now to be described with reference to the drawings of FIGS. 1 through 30.

FIG. 1 is a schematic perspective view of a first exemplary embodiment of the invention. Osteosynthesis plate 10 consisting of a first segment 1 and a second segment 2 can be seen attached to a bone 4.

Opposite to second segment 2 yet another segment is provided.

First segment 1 is substantially configured as a bone plate such as those known from prior art, having a main extension direction along which a plurality of passages 5 are provided.

In this exemplary embodiment, passages 5 are passages which enable an angularly stable connection by means of bone screws 30, and which may moreover be used for compression to close a fracture gap. Such a system is described in published patent application DE 10 2010 025001 A1.

According to the invention, the second segment 2 is movably attached to the first segment 1 by means of hinges 3.

Second segment 2 has two passages 6 for introducing bone screws 7 and extends transversely to the main direction of extension of the first segment.

Due to the connection by means of hinges 3, the osteosynthesis plate defined by segments 1 and 2 is able to follow the curved contour of the bone 4.

Furthermore, segment 2 is only movable in one degree of freedom relative to segment 1, namely pivotable about hinges 3.

In the axial direction, however, that is transversely to a possible breakage edge of bone 4, segments 1 and 2 are not movable.

The wing-like protruding segment 2 may therefore be used as a further additional fixing point for a bone screw.

Figure 2:
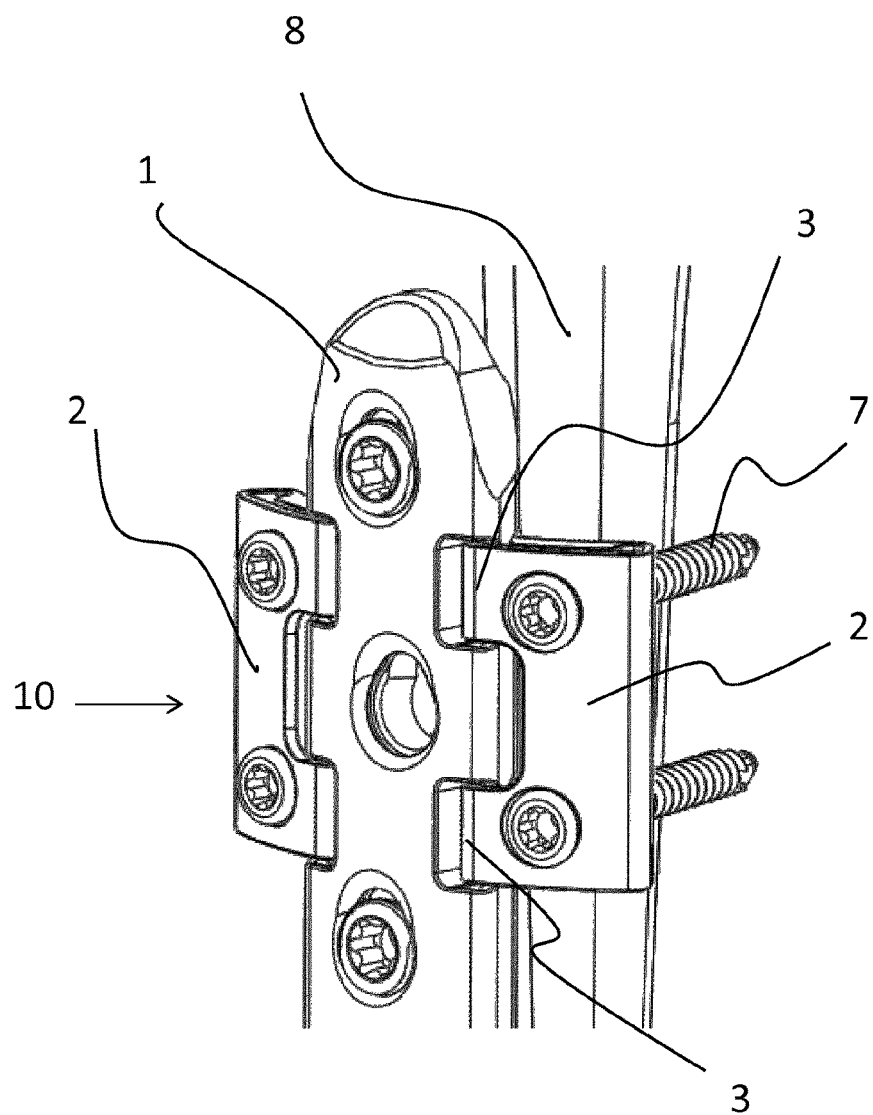

Referring to FIG. 2, functionality will be explained for the case of periprosthetic osteosynthesis.

FIG. 2 shows a detail of the osteosynthesis plate 10 illustrated in FIG. 1, consisting of first segment 1 and two further segments 2. Segments 2 protruding like wings through hinges 3 allow to introduce bone screws 7 which extend laterally of the medullary canal of the bone and thus past a prosthesis 8.

Besides a periprosthetic treatment, the additional segments 2 may also be used to provide additional fixing points in case of fragile bone material, in particular for older patients.

Figure 3:
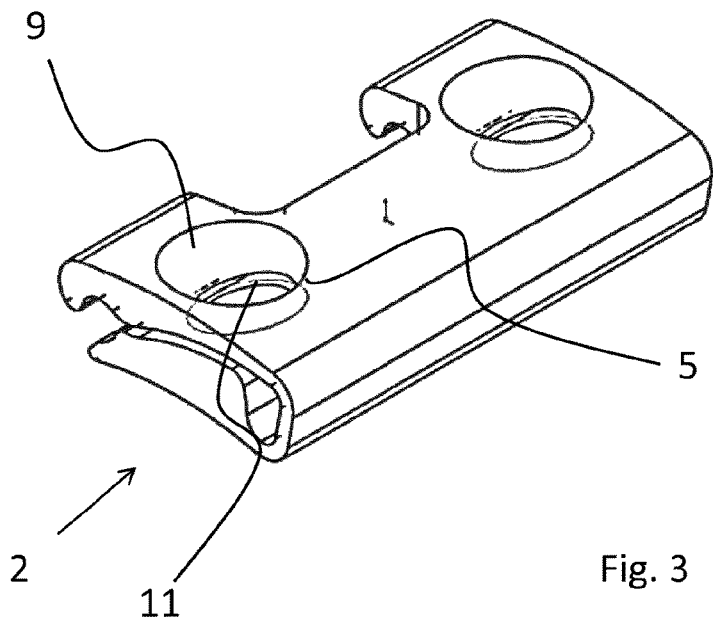

FIG. 3 shows a perspective view of a second segment 2.

Segment 2 is U-shaped and has a passage 5 with a smooth-walled section in an upper portion and a threaded section 11 in a lower portion.

Figure 4:
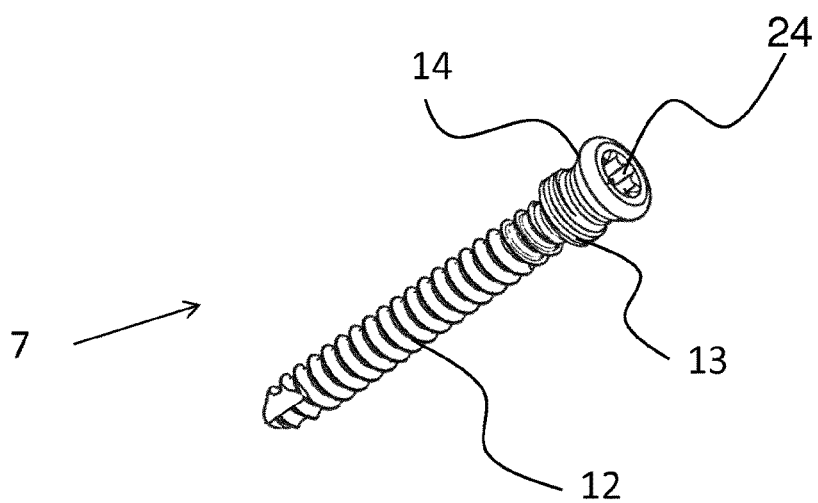

Segment 2 is adapted for cooperating with the bone screw shown in FIG. 4.

Bone screw 7 comprises a thread 12 for screwing into the bone, and a screw head 24 which has means for screwing in the screw using a handling tool.

Furthermore, bone screw 7 has a head thread 13 above thread 12, and has a bearing surface above the head thread, which is formed as a tapering portion 14 that may in particular have a conical or spherical shape.

Head thread 13 has a diameter of a size between the diameter of thread 12 and the diameter of screw head 24.

Figure 5:
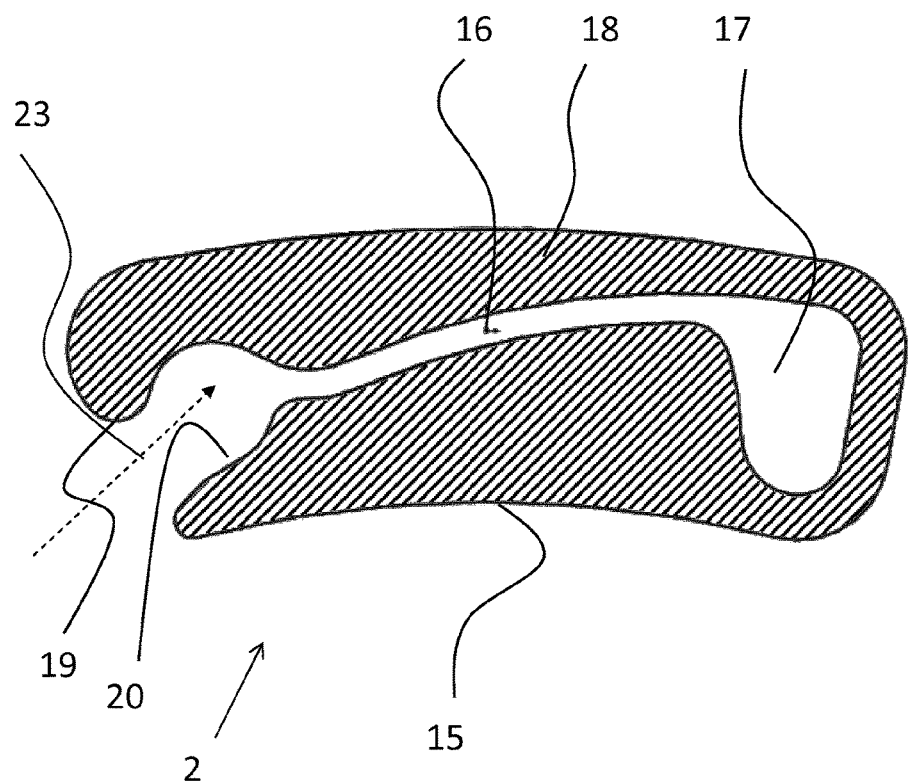

FIG. 5 shows a sectional view of the second segment shown in FIG. 3.

It can be seen that the second segment 2 is U-shaped, that means it is divided into a lower half 15 and an upper half 18.

Lower half 15 has a concave lower surface so as to better conform to the contour of the bone.

Upper half 18 and lower half 15 are separated by a recess 16.

Recess 16 first widens slightly in a front region which includes a hinge wing 19 and an indentation 20, so that this front region has a clamp-like shape to be adapted to be pressed onto a pin-shaped web of another segment (not illustrated).

Hinge wing 19 is formed so that it is able to enclose a web at least partially.

In order to allow to snap more easily onto a web without the need of tools, all the edges of the front region are rounded.

Moreover, the clamp-shaped region of recess 16 is inclined toward the lower half 15 so that the insertion direction as symbolized by an arrow 23 extends obliquely to the upper and lower surfaces of segment 2.

Behind the clamp-like region formed by hinge wing 19 and indentation 20, the recess 16 narrows and rises toward the upper half 18 of segment 2 so that the upper half 18 tapers toward the closed end.

Then, recess 16 widens toward the closed end of segment 2 so defining a bend portion 17 in which the upper half 18 is folded downwards, i.e. changes direction to merge into the lower half, so that the segment as a whole is U-shaped.

In this manner, the second segment 2 is designed as a clip having an upper half 18 and a lower half 15 which are resiliently deflectable relative to each other, so that the second segment 2 can be snapped onto a web with its front clamp-like region.

Figure 6:
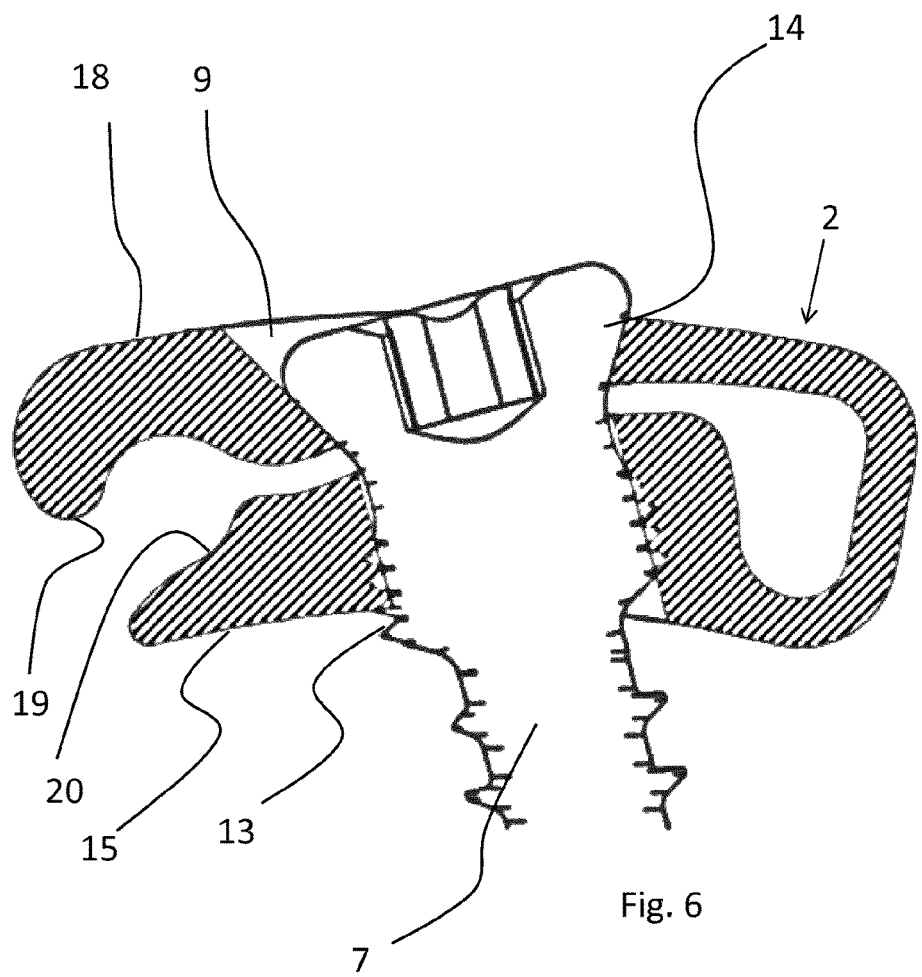

FIG. 6 shows a further sectional view of segment 2, illustrating the cooperation with bone screw 7.

Bone screw 7 introduced in the passage of segment 2 has a head thread 13 which corresponds to a thread of the passage in the lower half 15 thereof.

Above thread 13, screw 7 has a conical portion 14 which has a larger diameter than the thread.

Conical portion 14 engages a smooth-walled portion 9 of the passage in the upper half 18 of second segment 2.

If now the screw is further screwed in, it will draw the upper half 18 and the lower half 15 of the second segment to one another, so that hinge wing 19 and indentation 20 are moved toward each other.

If a web (not shown) is arranged between the hinge wing and the indentation, the second segment will be fastened on this web with a force-locked connection, so that the segments of the bone plate are not movable relative to each other.

Besides the function of fastening on a corresponding web, a result of the fixing of clip-like segment 2 moreover is that the upper and lower halves cannot deflect from each other so that the segment is prevented from sliding off the web.

Figure 7:
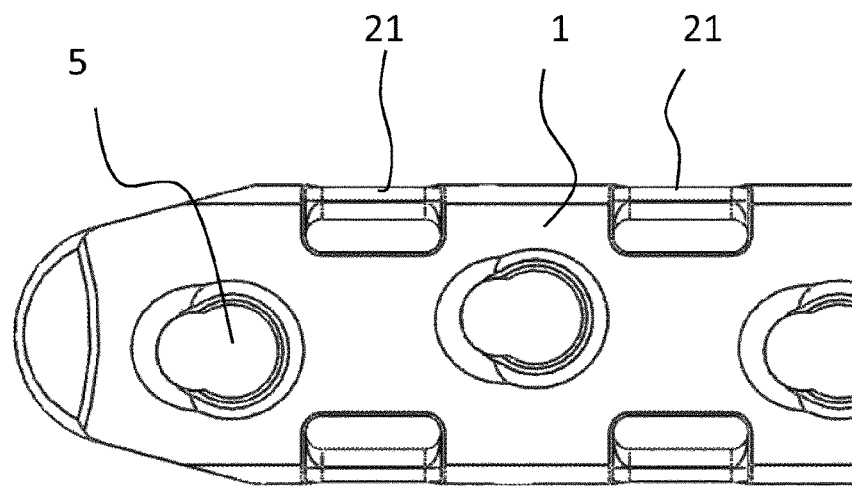

FIG. 7 shows a detail of a first segment 1, which is substantially formed as a bone plate having passages 5.

On its lateral sides, the bone plate has a plurality of recesses, each of which are bridged by a web 21.

Figure 8:
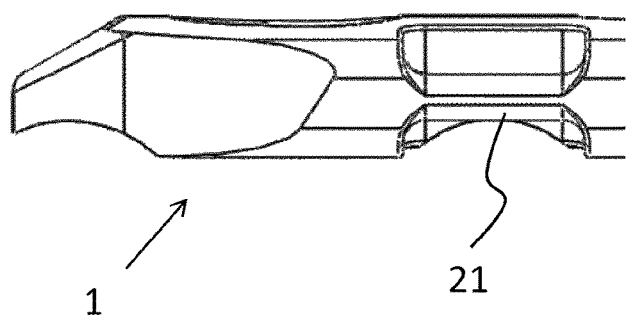

Web 21, which can be seen in a side view in FIG. 8, has a substantially circular cross section and is spaced both from the upper and lower surfaces of the bone plate.

If now a second segment (not shown) is added, it will be approximately flush with the first segment 1.

Figure 9:
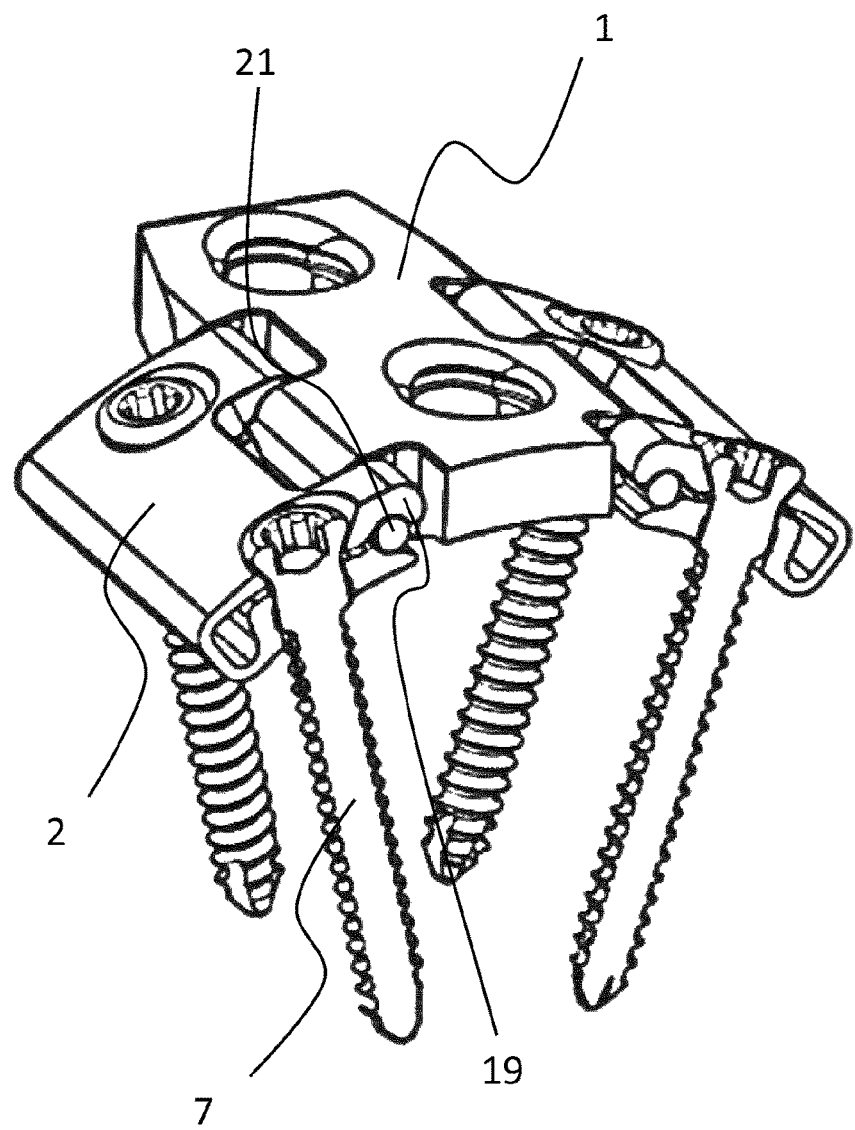

FIG. 9 shows a perspective sectional view of an osteosynthesis plate.

The first segment 1 can be seen therein. The second segment 2, which has a clip-like configuration, has been urged onto the web 21 of first segment 1.

By tightening bone screw 7, which has a head thread, first segment 1 and second segment 2 are now fixed relative to each other.

Figure 10:
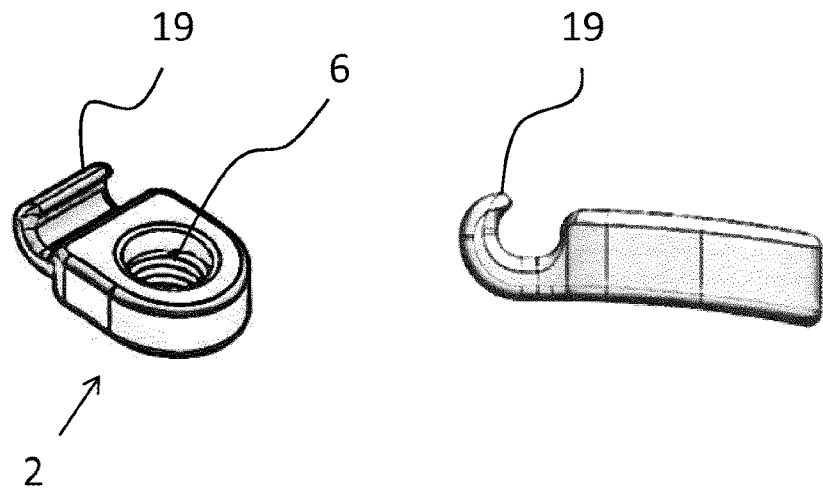

FIG. 10 shows an alternative embodiment of a second segment.

The second segment 2 has a passage 6 which is threaded in this exemplary embodiment, and has a hook-shaped hinge wing 19.

With the hook-shaped hinge wing 19, the second segment 2 may be slid onto the bone plate shown in the preceding drawings and will be hooked there. A positive locking connection is produced, which may however be released by pivoting the second segment upwards and pulling it sidewards.

In this exemplary embodiment, the second segment 2 is adapted for engaging a single web only.

Figure 11:
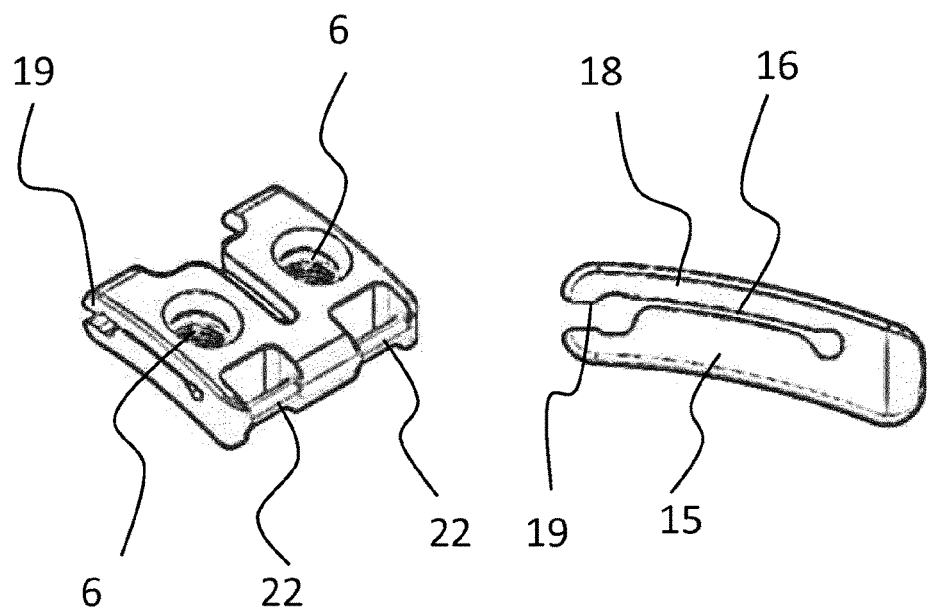

FIG. 11 shows a another embodiment of a second segment which has a clip-like configuration with two hinge wings 19 and two passages 6 which substantially correspond to those of the embodiment illustrated in FIG. 3.

In contrast to the embodiment shown in FIG. 3, the segment of FIG. 11 is a double hinge, since on the side opposite the hinge wing the second segment has two webs 22 to which a further segment may be pivotally attached.

As is clearly visible in the sectional view shown on the right, hinge wing 19 defines a clamp-like region, and the segment is divided into a lower half and an upper half 18 which are separated by recess 16. Thus, the segment is U-shaped.

Figure 12:
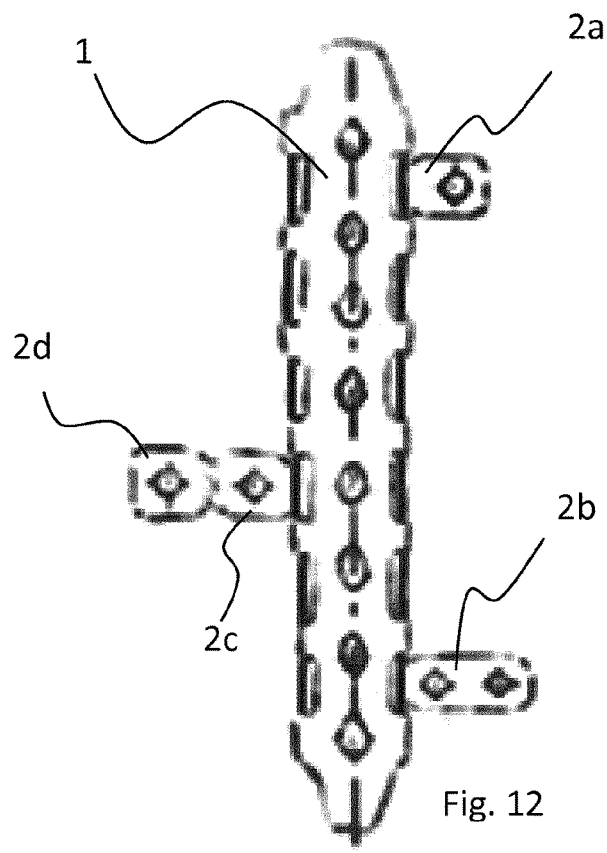

FIG. 12 schematically shows a first segment 1 in form of a bone plate, which has webs spaced apart substantially over the entire length, to which segments 2a, 2b, 2c, 2d may be attached.

It can be seen that segments 2a to 2d may be attached at different sites of the first segment 1.

Furthermore, it is possible to attach different segments, depending on the indication. For example, segment 2a is shorter and has only one passage. Segment 2b is longer and has two spaced-apart passages.

Segments 2c and 2d form a link chain with segment 1.

Figure 13:
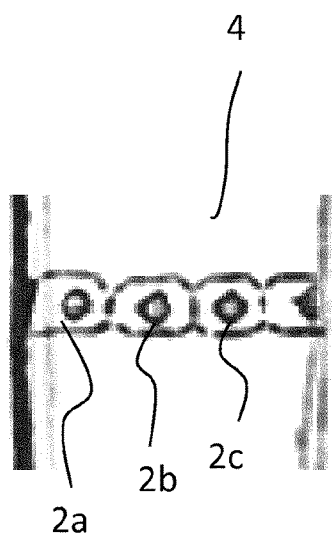

As illustrated in FIG. 13, segments 2a to 2c may form a chain by means of which a bone 4 may be wrapped fully or partially.

Figure 14:
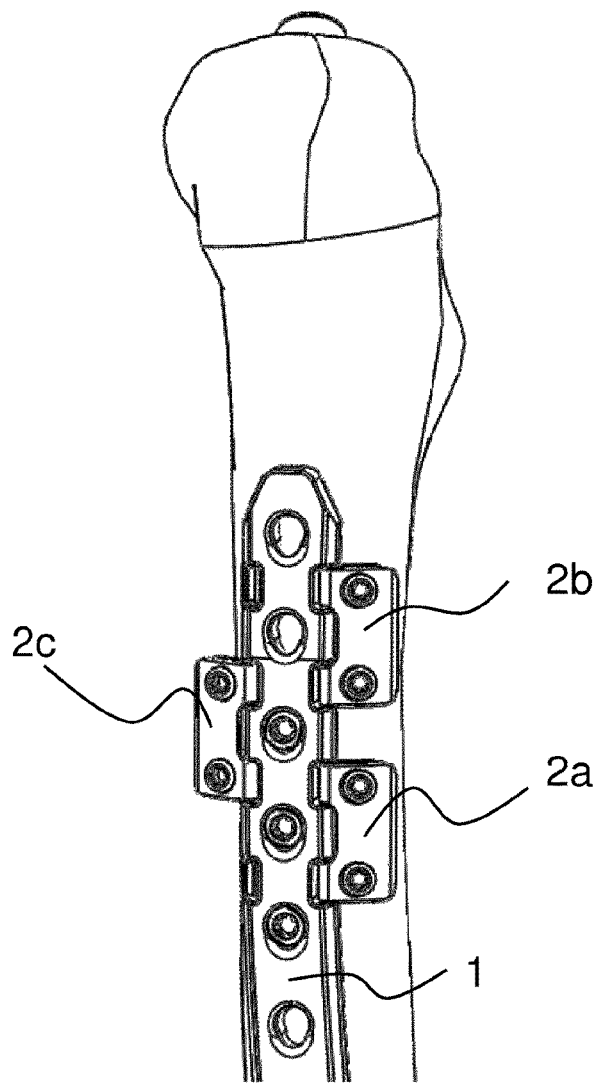

FIG. 14 shows another embodiment of the invention, namely an osteosynthesis plate bearing on the surface of a bone and consisting of segment 1 in form of an elongated bone plate having a plurality of passages, and segments 2a to 2c laterally attached thereto.

In contrast to the embodiment variant shown in FIG. 1, segment 2c is arranged offset relative to segments 2a and 2b.

For this purpose, the first segment has a plurality of sites at which further segments may be attached.

Figure 15:
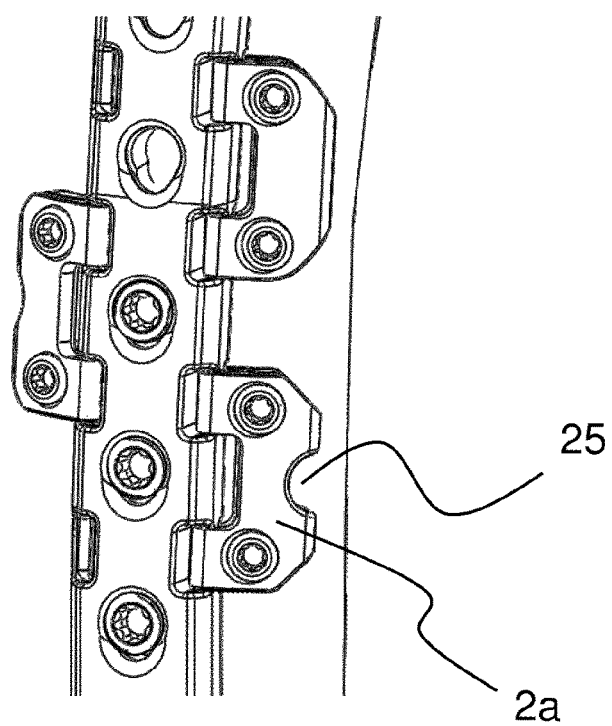

FIG. 15 shows a further embodiment, which substantially corresponds to that of FIG. 14.

In contrast to FIG. 14, segment 2a has a lateral recess 25 which may serve as a guiding groove for a cerclage cable, for example.

Figure 16:
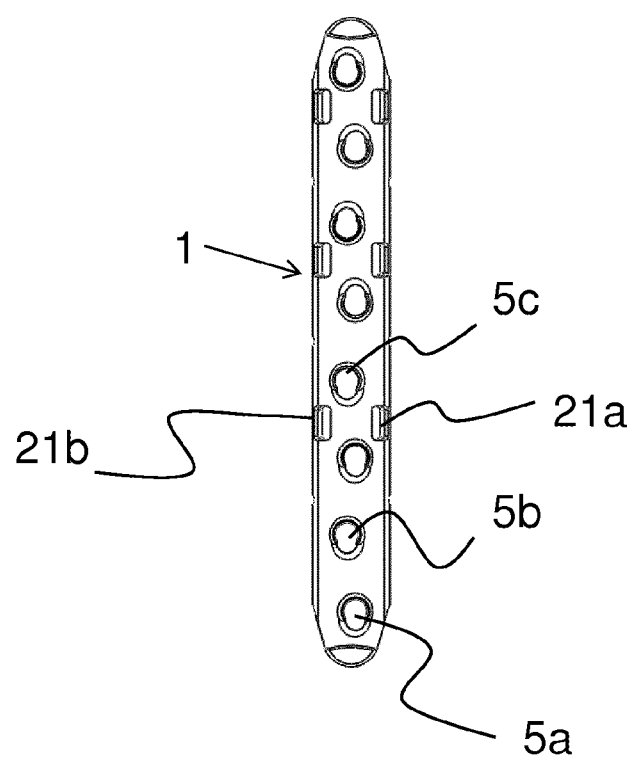

FIG. 16 shows a further variant of a first segment 1.

Segment 1 has a plurality of opposing webs 21a, 21b, to which further segments may be attached.

Moreover, the first segment 1 has a plurality of passages 5a to 5c.

These passages are each offset relative to one another transversely to the main direction of extension of the first segment.

Figure 17:
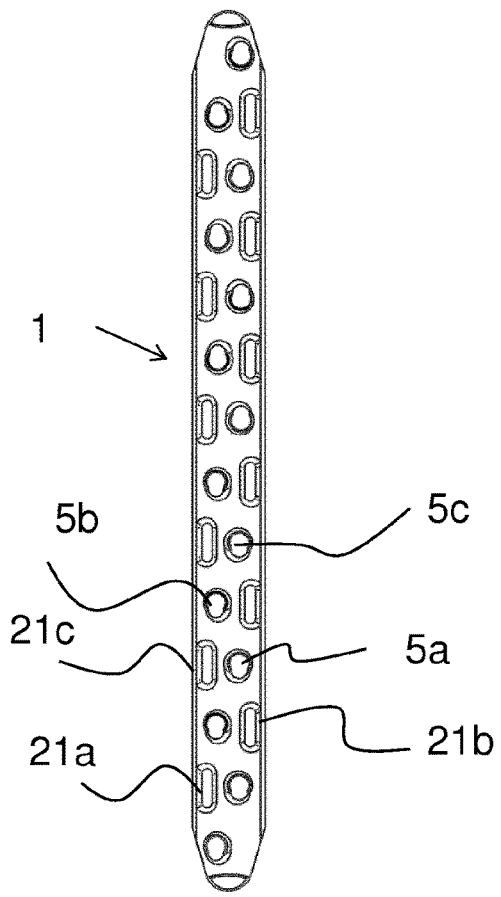

FIG. 17 shows another embodiment variant of a first segment 1.

Passages 5a to 5c are disposed offset relative to one another transversely to the main direction of extension, alternately to the right and to the left direction.

Next to each passage, a web 21a to 21c is arranged, for mounting a second segment. Thus, webs 21a to 21c are also offset to the right and to the left, i.e. transversely to the main direction of extension.

This embodiment allows for a particularly slim design of a first segment 1.

Figure 18:
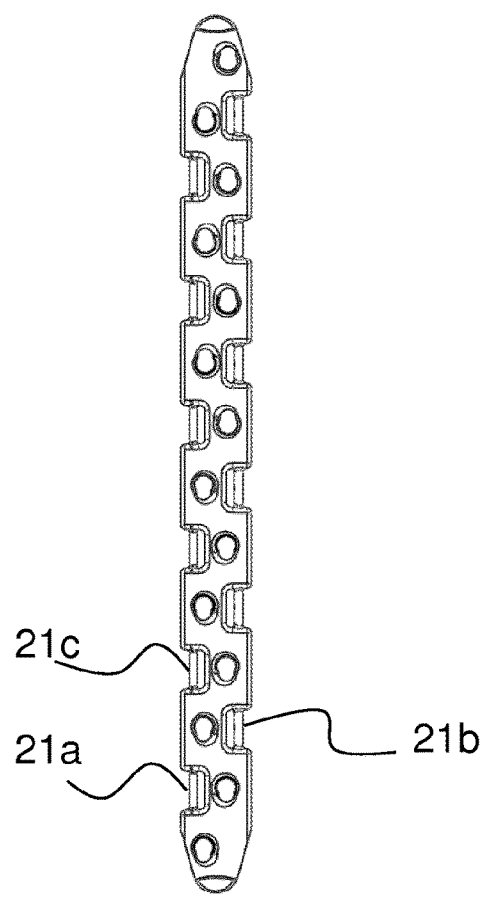

The embodiment variant shown in FIG. 18 substantially corresponds to that of FIG. 17, with the difference that webs 21a to 21c are arranged not exactly flush to the edge but offset towards the center of the first segment 1. Thus, the pivot point is shifted towards the center of the plate, allowing for an even slimmer design with laterally attached further segments.

Figure 19:
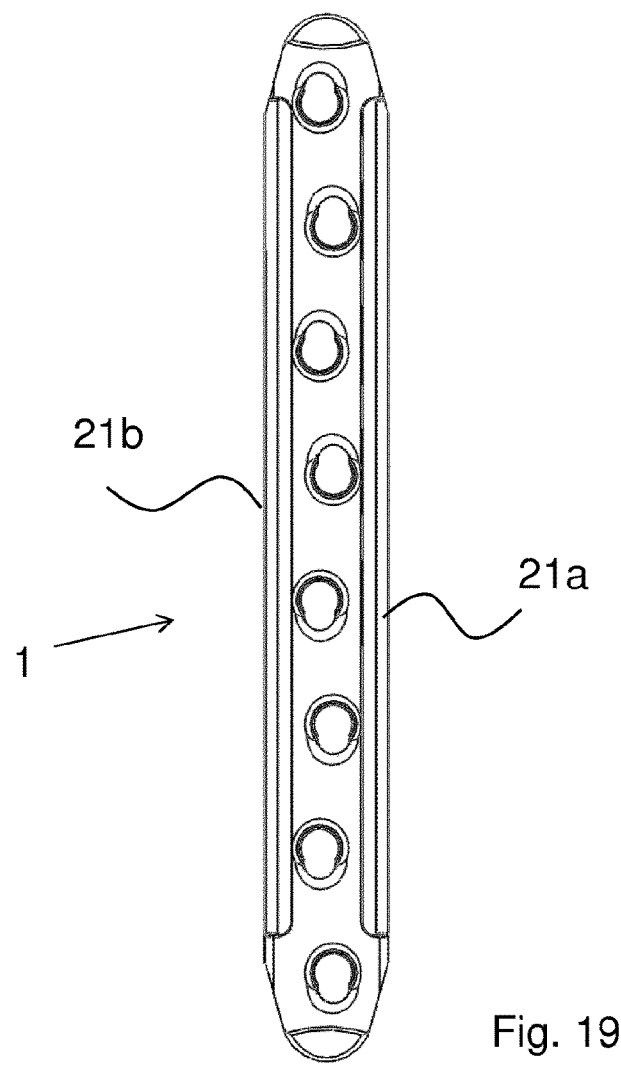

FIG. 19 shows a further embodiment of a first segment.

This embodiment variant also has opposite lateral webs 21a and 21b, which in this case occupy a majority of the length of the bone plate.

Therefore, segments (not shown) which can be attached to this first segment, may be displaced in the axial direction of webs 21a, 21b.

Therefore, this embodiment is particularly suitable in conjunction with the fixable segments as previously illustrated.

Figure 20:
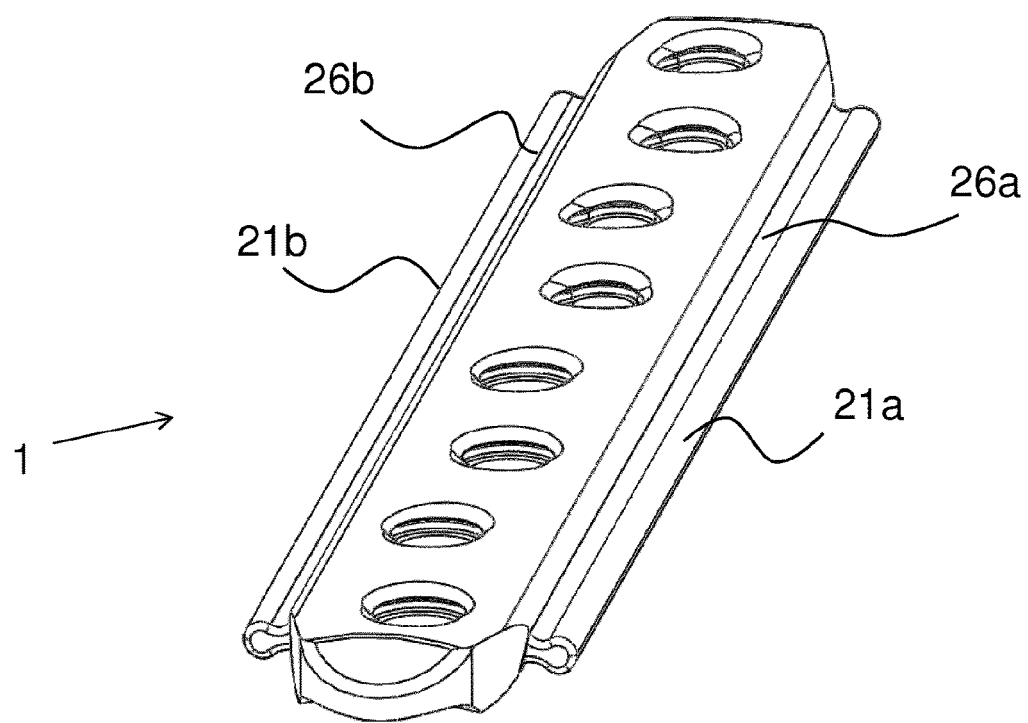

FIG. 20 shows a further embodiment of a first segment.

This embodiment variant also includes opposite lateral webs 21a and 21b, which occupy a majority of the length of the bone plate.

In order to achieve better stability, among other things, there is no recessed area between the edge-side webs 21a and 21b and the segment, rather the webs are provided in form of rails 26a, 26b.

As a result, adjustability of the angle may be limited, i.e. the second segment (not shown) might be adjustable in a smaller angular range.

In addition to an increased stability, it is moreover easily possible in case of such a rail-like system to attach the second segment not by snapping like a clip but by sliding it onto the rail in the direction of the main extension direction of the first segment.

Figure 21:
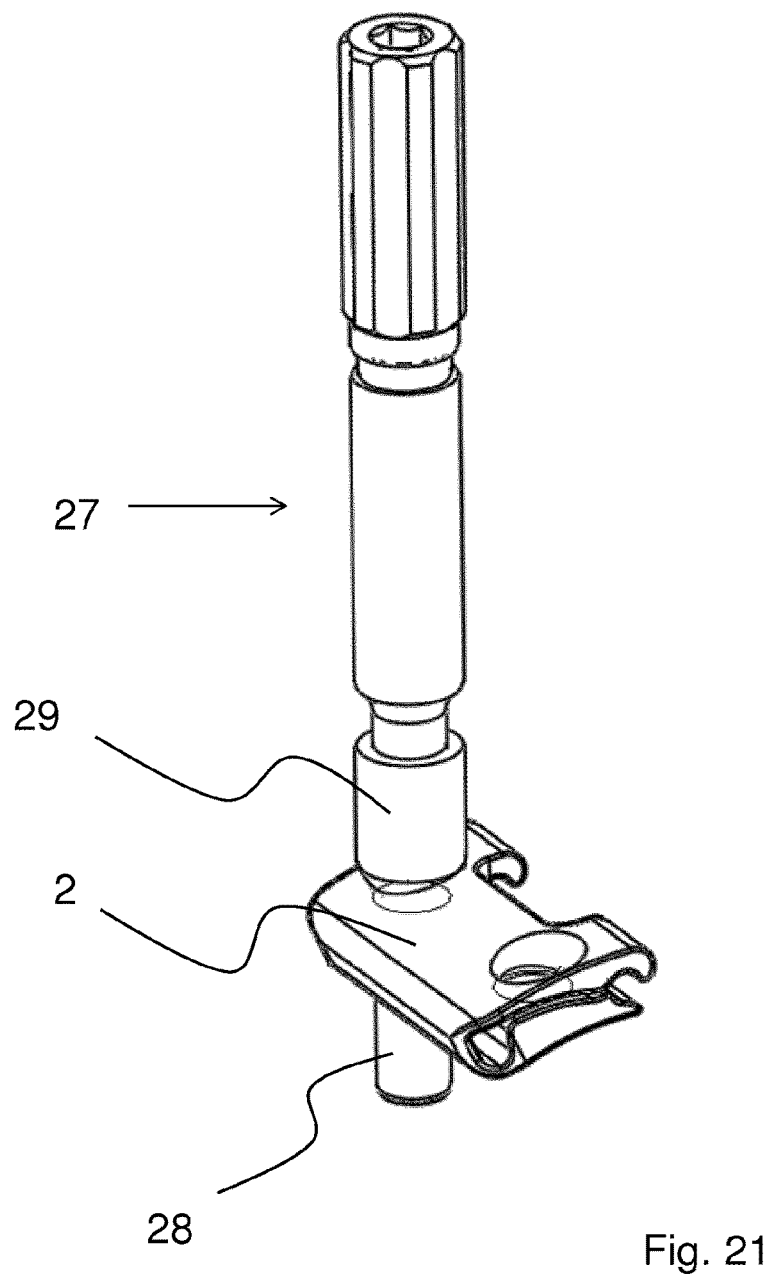

With reference to FIG. 21 it shall be explained how two segments can be fixed relative to each other with angular stability by means of a drill sleeve.

A segment 2 can be seen, which essentially corresponds to the segment illustrated in FIG. 3.

Another segment to which segment 2 is to be attached is not shown for the sake of clarity.

A drill sleeve 27 is screwed into a passage of segment 2.

For this purpose, the drill sleeve has a thread 28 which can be screwed into the thread of the lower half of segment 2.

Otherwise, the drill sleeve has a central channel and serves as a targeting device for a drill.

The drill sleeve further comprises a locking nut 29 which sits on thread 28.

When a desired angle is obtained, locking nut 29 may be tightened and will then press onto the upper surface of segment 2 to push the two halves of segment 2 together so that the latter will be clamped on another segment with angular stability.

In another variant, in which the angle is not adjusted through the depth to which the drill sleeve is screwed in, it is conceivable that the halves of the segment are drawn together directly by the thread of the drill sleeve. The illustrated locking nut 29 would then not be formed as a nut, but rather as a thickened portion of the drill sleeve, as compared to the thread.

Figure 30:
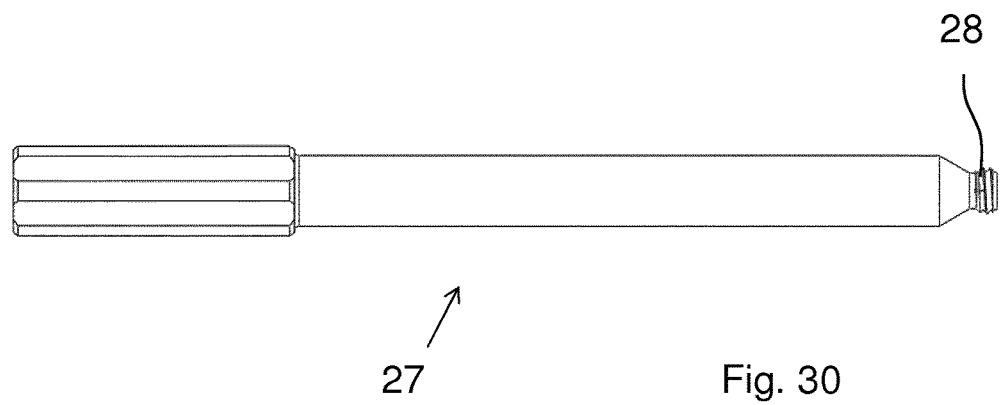

Such an embodiment is shown in FIG. 30. Drill sleeve 27 has a thread 28 for screwing into a segment. When screwing in the drill sleeve 27, a bearing surface which is disposed above thread 28 and which is conical in this exemplary embodiment, will engage the upper surface of the segment and will draw the halves of the segment together (not shown).

In the embodiment shown in FIG. 21, by contrast, the angle may first be adjusted due to the fact that for a different screwing depth the lower end of the drill sleeve will protrude to different extents from the lower surface of segment 2.

The lower end of the drill sleeve will abut on the bone (not shown), so that the distance of the segment 2 to the bone and thus the angle relative to another segment (not shown) can be adjusted depending on the depth to which the drill sleeve is screwed in.

The drill sleeves shown in FIGS. 21 and 30 provide for an angularly stable connection already when introducing a bore into the bone.

Figure 22:
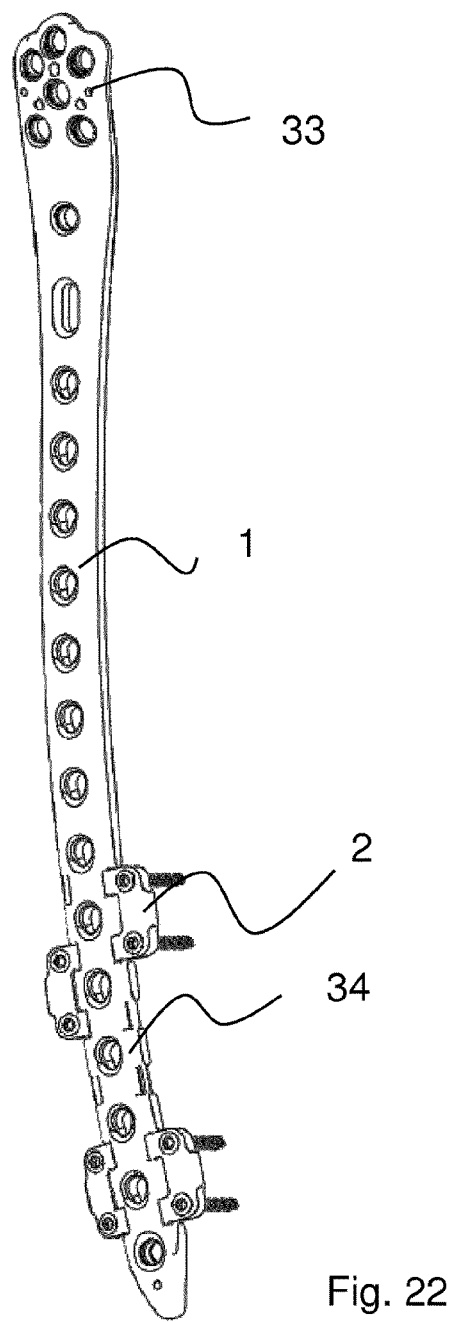

FIG. 22 shows a further embodiment of the invention.

A first segment 1 can be seen, which is formed as an elongated bone plate.

In this exemplary embodiment, in order to conform to the bone, the first segment 1 in the form of a bone plate is curved both in a plane in parallel to the bone and in a plane perpendicular thereto.

Furthermore, the first segment 1 has an enlarged head 33 which is used to be applied to the thicker end of the bone.

In contrast to the portion below which is intended for the shaft of the bone, a plurality of passages for bone screws may be arranged side by side in the head 33.

In a lower region 42, a plurality of webs are provided, which serve to fix second segments 2 as has already been illustrated in the previous drawings.

Figure 23:
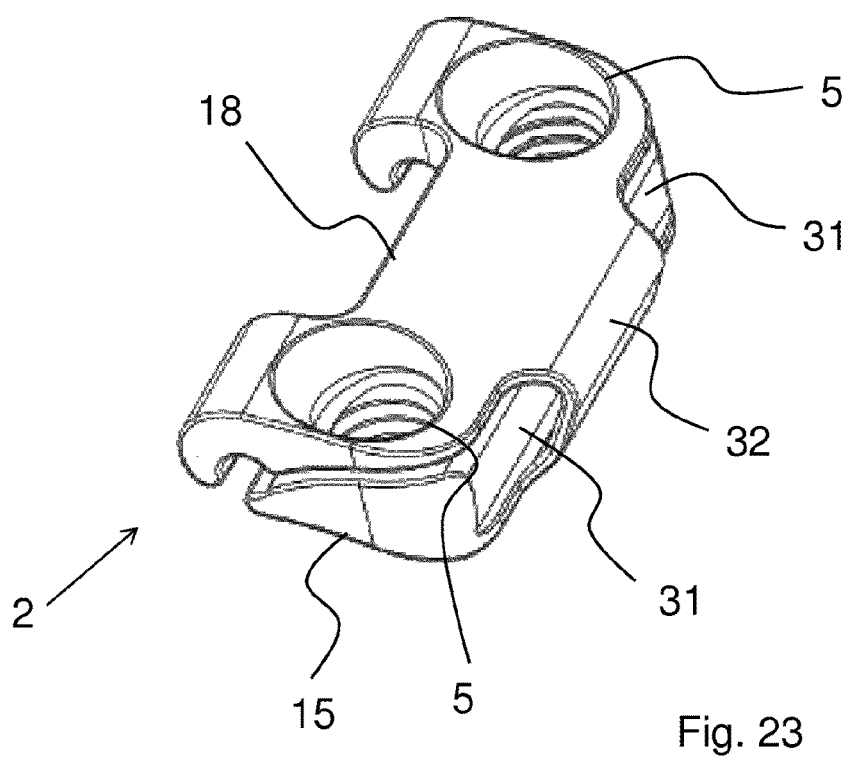

FIG. 23 shows another embodiment variant of a segment 2.

This segment is adapted for being attached to a bone plate and itself has two passages 5 for bone screws.

In contrast to the segment illustrated in FIG. 2, the connecting portion 32 which connects the upper half 18 with the lower half has two recesses 31 on either end thereof.

Due to the recesses 31, the connecting portion 32 is weakened, so that less force has to be exerted compared to an embodiment without recesses to push apart the upper half 18 and the lower half 15.

It will be understood that a similar effect may also be achieved when the connecting portion 32 is formed thinner than the upper and lower halves, for example. However, the recesses 31 and the associated optionally thicker configuration of the connecting portion 32 allows for easier manufacturing, in particular when segment 2 is made from solid material.

Moreover, segment 2 is more robust in this way.

It will be understood that in particular in this embodiment when forcing apart the upper half 18 and the lower half 15 a deformation will mainly occur in the connecting portion 32, whereas the upper half 18 and the lower half 15 are thicker than the connecting portion 32 and therefore do not or only little contribute to the resilient behavior.

Thus, upper half 18 and lower half 15 are thick and therefore robust in particular in the region of passages 5.

Figure 24:
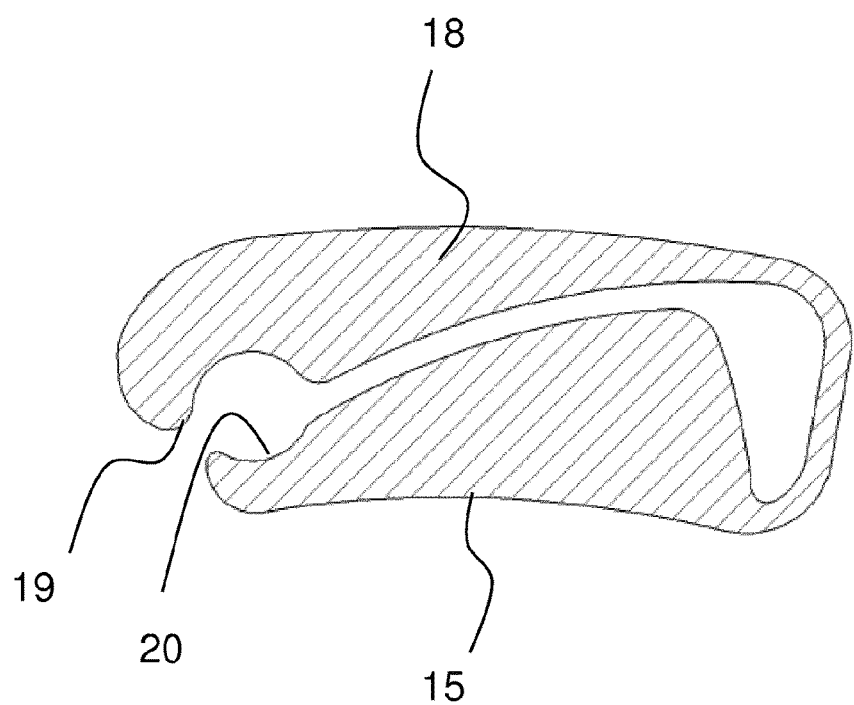

FIG. 24 shows a sectional view of the embodiment variant of a second segment as illustrated in FIG. 23.

In contrast to the embodiment variant illustrated in FIG. 5, the indentation 20 in lower half 15 is more pronounced.

The opposite hinge wing 19 and indentation 20 define a substantially circular region between the upper half 18 and the lower half 15, in which a web of the first segment will be arranged in the snapped-in state.

This segment, too, is snapped obliquely from above onto the other segment which is preferably formed as a bone plate.

Figure 25:
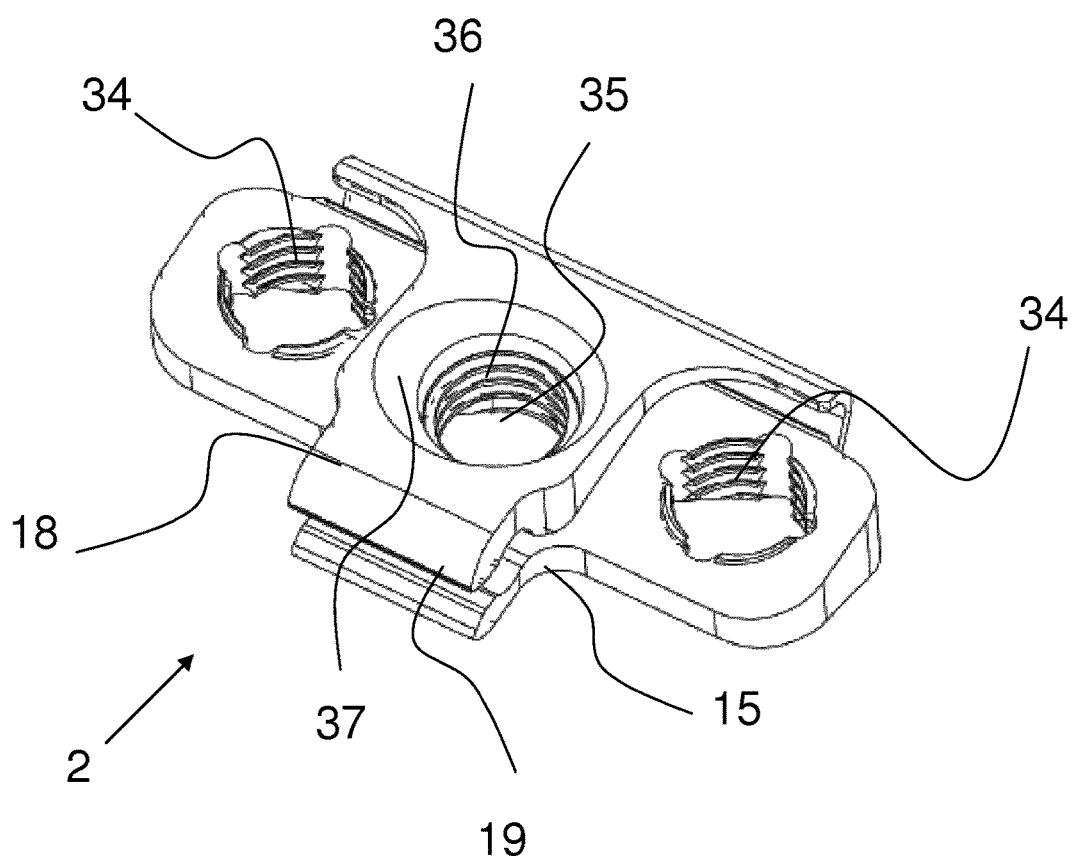

FIG. 25 shows a further alternative embodiment variant of a second segment 2.

In this embodiment variant, locking of the segment and introducing of bone screws are decoupled from each other.

This segment 2, again, has a clip-like configuration and has a lower half 15 and an upper half 18.

In this embodiment variant, threads 34 for introducing bone screws are only provided in the lower half. Instead of a thread, a passage without thread may optionally be provided.

Furthermore, segment 2 comprises a further passage 35 which is intended for locking the segment 2.

Passage 35 comprises a thread 36 provided in the lower half 15, and a bearing surface 37 in the upper half 18.

Bearing surface 37 has a conical shape in this exemplary embodiment. However, it is likewise conceivable, for example, that simply the upper surface of upper half 18 serves as a bearing surface.

The segment in form of a clip may be snapped onto a web of a bone plate and may then be locked already before being applied.

Figure 26:
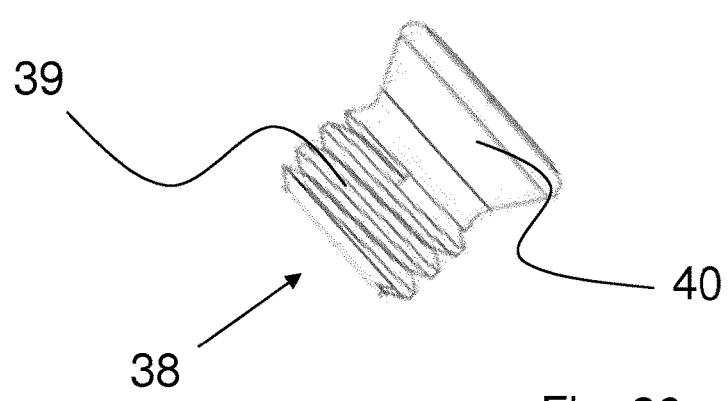

For this purpose, a screw 28 as shown in FIG. 26 may be used.

This screw is not a bone screw, that means it does not have a thread for screwing into the bone.

Rather, thread 39 is adapted to be screwed into the thread in the lower half of the segment shown in FIG. 25. The bearing surface 40 on the screw head engages the bearing surface 37 of the segment illustrated in FIG. 25 and while being screwed in draws together the upper and lower halves of the segment, so that the latter is locked on the web of a bone plate.

The segment illustrated in FIG. 25 has one central hinge wing 19.

Figure 27:
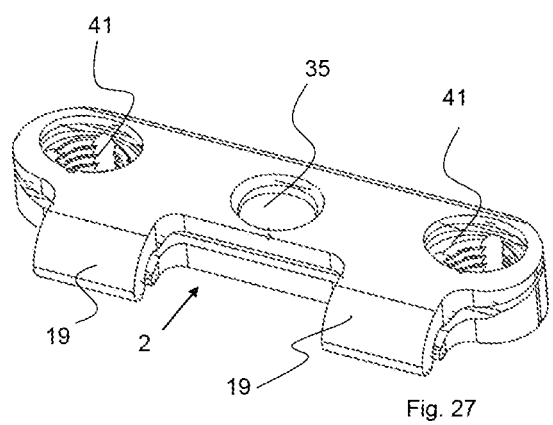

FIG. 27 shows a further embodiment variant in which the segment 2 may already be locked prior to application.

Like the embodiment variant shown in FIG. 25, the segment 2 comprises a passage 35 corresponding to that of the embodiment variant in FIG. 25 and by means of which the segment 2 may be locked before application and before bone screws are screwed in.

In this exemplary embodiment, passages 41 each comprise a thread and are intended for introducing a bone screw.

It is moreover conceivable to additionally use the passages 41 for locking, that is to say that when a bone screw is screwed in, the upper and lower halves are further drawn together and so the locking is intensified. However, this is not necessary.

In this exemplary embodiment, segment 2 includes two spaced apart hinge wings 19 between which passage 35 is located which is intended for inserting a screw that is exclusively used for locking.

Figure 28:
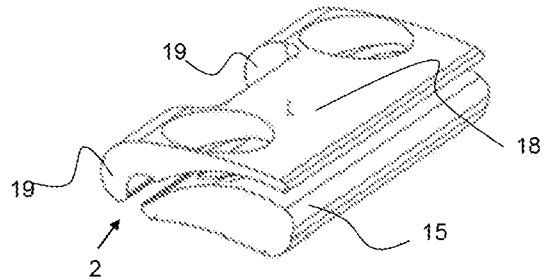

FIG. 28 shows a further embodiment of a segment.

In contrast to the previously illustrated segments, this segment does not has a clip-like configuration, i.e. it cannot be attached by snapping, rather the upper and lower halves 18, 15 are separate parts.

Otherwise, the segment has a configuration similar to the segment illustrated in FIG. 3.

The segment 2 of FIG. 28 includes two spaced apart hinge wings 19.

Figure 29:
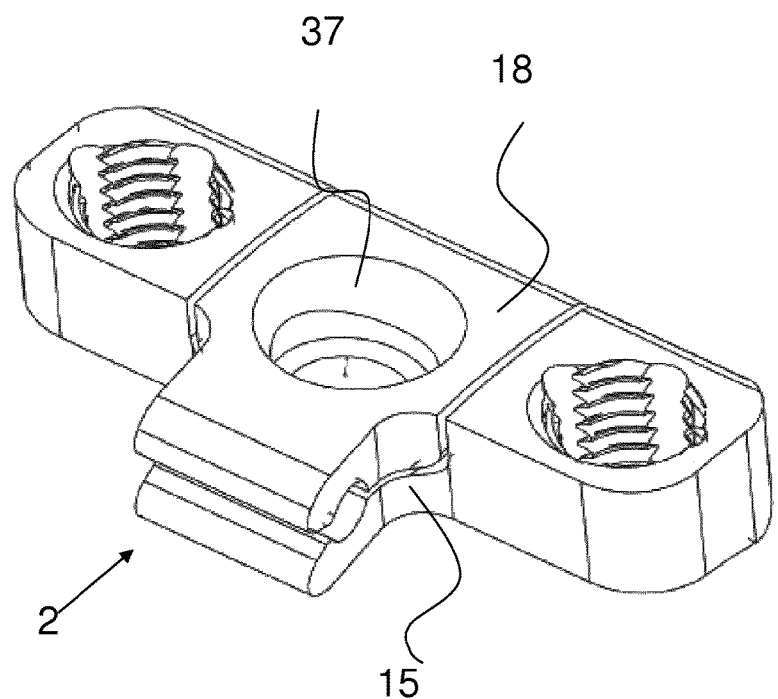

FIG. 29 shows a further embodiment in which the segment 2 is not configured like a clip.

In this embodiment variant, locking and introducing of bone screws are decoupled, similar to the embodiment variant of FIG. 25.

The segment 2 of FIG. 29 comprises a centrally inserted upper part 18 which has a bearing surface 37 and which is exclusively intended for locking segment 2 to a bone plate.

In this exemplary embodiment, the lower part 15 has a greater thickness adjacent to the upper part 18, so that at the ends of the lower part the upper surface thereof is flush with the central region in which the upper part 18 is inserted.

The invention allows in a very simple way to provide an osteosynthesis plate for flexible applications. In particular it enables to improve the osteosynthesis of periprosthetic fractures.

LIST OF REFERENCE NUMERALS

1 First segment
2 Second segment
3 Hinge
4 Bone
5 Passage
6 Passage
7 Bone screw
8 Femoral prosthesis 9 Smooth-walled portion
10 Osteosynthesis plate
11 Threaded portion
12 Thread
13 Head thread
14 Conical portion
15 Lower half
16 Recess
17 Bend portion
18 Upper half
19 Hinge wing
20 Indentation
21 Web
22 Web
23 Arrow
24 Screw head
25 Recess
26 Rail
27 Drill sleeve
28 Thread
29 Locking nut
30 Bone screw
31 Recess
32 Connecting portion
33 Enlarged head
34 Thread
35 Passage
36 Thread
37 Bearing surface
38 Screw
39 Thread
40 Bearing surface
41 Passage
42 Lower portion

The invention claimed is:

1. An osteosynthesis system, comprising:
a first segment and a second segment;
at least the first segment having a web;
at least the second segment having a passage for a screw;
wherein the second segment is releasably connectable to the first segment;
wherein an angle in which the first and second segments are arranged relative to one another can be modified;
wherein the second segment is snapped onto the web of the first segment;
wherein the second segment has an upper half and a lower half, the passage extending through an uppermost surface of the upper half, the upper half, the lower half, and a lowermost surface of the lower half, the second segment configured to be fastened on the web of the first segment with a force-locked connection by moving the upper and lower halves toward each other; and
wherein the upper and the lower halves of the second segment are moved towards each other by introducing the screw into the passage extending through the upper and lower halves of the second segment.

2. An osteosynthesis system, comprising an osteosynthesis plate with at least one passage for a bone screw and further comprising:
a drill sleeve insertable into the at least one passage and having a thread for screwing into the at least one passage;
wherein the drill sleeve is configured so that when the drill sleeve is screwed into the at least one passage, a lower end of the drill sleeve protrudes beyond a lower surface of the osteosynthesis plate, wherein depending on the extent of screwing into the at least one passage the lower end of the drill sleeve abuts against bone to permit adjustment of a spacing between the osteosynthesis plate and the bone or an angle between a first segment of the osteosynthesis plate and a second segment of the osteosynthesis plate, which includes upper and lower halves, the at least one passage extending through an uppermost surface of the upper half of the second segment, the upper half of the second segment, the lower half of the second segment and a lowermost surface of the lower half of the second segment, the second segment connected with the first segment of the osteosynthesis plate;
wherein the drill sleeve comprises means for drawing together the upper and lower halves of the second segment.

3. The osteosynthesis system, comprising the osteosynthesis plate as claimed in claim 2, further comprising a bone screw adapted for fixing the first and second halves of the second segment to one another when the bone screw is screwed in.

4. An osteosynthesis system, comprising:
a bone plate or a segment of a bone plate, the bone plate or the segment of the bone plate having:
upper and lower halves defining a clip-like configuration for snapping on a web of another bone plate or another segment of a bone plate;
at least one passage extending through the upper and lower halves, wherein a portion of the at least one passage extending through the lower half has a thread; and
a bone screw having a thread and a screw head with a bearing surface, which has a head thread between the thread and the screw head;
wherein the head thread of the screw is adapted for engaging the thread of the portion of the at least one passage extending through the lower half; and
wherein the bearing surface of the bone screw abuts at a portion of the at least one passage extending through the upper half when being screwed in, so that the upper and lower halves are drawn together.

5. The osteosynthesis system as claimed in claim 4, further comprising a drill sleeve introducible into the at least one passage, wherein the drill sleeve comprises means for drawing together the upper and lower halves of the bone plate or the segment of the bone plate.

6. An osteosynthesis system comprising:
a bone plate; and
a segment;
wherein the bone plate includes a plurality of passages for bone screws and a web;
wherein the segment includes at least one passage for a screw;
wherein the segment has upper and lower halves defining a clip-like configuration for allowing the segment to be snapped onto the web of the bone plate, the at least one passage extending through the upper and lower halves;
wherein moving the upper and lower halves toward each other creates a force-locked connection with the web of the bone plate; and
wherein the upper and the lower halves are moved towards each other by introducing a screw into the at least one passage of the segment.

7. The osteosynthesis system as claimed in claim 6, wherein the clip-like segment is U-shaped.

8. The osteosynthesis system as claimed in claim 6, wherein the segment is pivotally movable relative to the bone plate.

9. The osteosynthesis system as claimed in claim 8, wherein the segment further includes a hinge for movably connecting with the web of the bone plate.

10. The osteosynthesis system as claimed in claim 6, wherein the bone plate and the segment are releasable and connectable without using tools.

11. The osteosynthesis system as claimed in claim 6, wherein the bone plate further includes at least a second web for receiving at least one hinge wing of the segment.

12. The osteosynthesis system as claimed in claim 6, wherein the segment has a web for receiving a hinge wing of another segment.

* * * * *